(12) United States Patent
Mayer et al.

(10) Patent No.: US 11,723,715 B2
(45) Date of Patent: Aug. 15, 2023

(54) SURGICAL INSTRUMENT COMPRISING ELECTRODE SUPPORT

(71) Applicant: ERBE ELEKTROMEDIZIN GMBH, Tuebingen (DE)

(72) Inventors: Volker Mayer, Tuebingen (DE); Achim Brodbeck, Metzingen (DE); Markus Schmid, Heiningen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 636 days.

(21) Appl. No.: 15/818,568

(22) Filed: Nov. 20, 2017

(65) Prior Publication Data
US 2018/0325581 A1 Nov. 15, 2018

Related U.S. Application Data

(62) Division of application No. 14/619,890, filed on Feb. 11, 2015, now Pat. No. 9,848,939.

(30) Foreign Application Priority Data

Feb. 12, 2014 (EP) ..................... 14154832

(51) Int. Cl.
*A61B 18/18* (2006.01)
*A61B 18/14* (2006.01)
*A61B 18/00* (2006.01)

(52) U.S. Cl.
CPC .. *A61B 18/1445* (2013.01); *A61B 2018/0063* (2013.01); *A61B 2018/00077* (2013.01); *A61B 2018/00089* (2013.01); *A61B 2018/00101* (2013.01); *A61B 2018/00107* (2013.01)

(58) Field of Classification Search
CPC ...... A61B 18/1445; A61B 2018/00077; A61B 2018/00089; A61B 2018/00101; A61B 2018/00107; A61B 2018/0063
See application file for complete search history.

(56) References Cited

U.S. PATENT DOCUMENTS

| 3,688,402 | A | * | 9/1972 | Shannon | ................. | B26B 13/04 |
| | | | | | | 30/260 |
| 3,750,282 | A | * | 8/1973 | Eaton | ................. | A61B 17/3201 |
| | | | | | | 24/28 |
| 5,697,949 | A | * | 12/1997 | Giurtino | ............ | A61B 18/1445 |
| | | | | | | 606/205 |
| 6,113,598 | A | | 9/2000 | Baker | | |

(Continued)

FOREIGN PATENT DOCUMENTS

| CN | 102860866 A | 1/2013 |
| CN | 102908192 A | 2/2013 |

(Continued)

*Primary Examiner* — Michael F Peffley
*Assistant Examiner* — Amanda L Zink
(74) *Attorney, Agent, or Firm* — Blank Rome LLP

(57) ABSTRACT

A branch of an instrument comprising a metal part, which is embodied in one piece seamlessly, which comprises the electrode support as well as the electrode plate and connection webs. Preferably, this metal part is produced in an additive production method, for example selective laser melting (SLM). The branches are suitable for instruments for open surgery as well as for laparoscopic and flexible endoscopic instruments.

19 Claims, 3 Drawing Sheets

(56) References Cited

U.S. PATENT DOCUMENTS

| | | | |
|---|---|---|---|
| 6,406,475 B1* | 6/2002 | Wenzler | A61B 18/1445 606/50 |
| 7,103,947 B2* | 9/2006 | Sartor | A61B 18/1445 29/527.1 |
| 7,166,106 B2 | 1/2007 | Bartel et al. | |
| 8,574,231 B2* | 11/2013 | Boudreaux | A61B 18/1445 607/99 |
| 2003/0158547 A1* | 8/2003 | Phan | A61B 18/14 606/41 |
| 2004/0049185 A1 | 3/2004 | Latterell et al. | |
| 2006/0095031 A1* | 5/2006 | Ormsby | A61B 18/1445 606/41 |
| 2009/0216228 A1 | 8/2009 | Masuda | |
| 2009/0248021 A1* | 10/2009 | McKenna | A61B 18/1445 606/51 |
| 2011/0251611 A1* | 10/2011 | Horner | A61B 18/1442 606/49 |
| 2011/0257680 A1 | 10/2011 | Reschke et al. | |
| 2013/0023875 A1* | 1/2013 | Harris | A61B 18/1445 606/41 |
| 2013/0035685 A1* | 2/2013 | Fischer | A61B 18/1445 606/41 |
| 2016/0038226 A1* | 2/2016 | Brandt | B29B 11/14 216/13 |

FOREIGN PATENT DOCUMENTS

| | | |
|---|---|---|
| DE | 10 2011 003 520 A1 | 8/2012 |
| EP | 0 572 131 A1 | 12/1993 |
| EP | 2 377 80 A1 | 10/2011 |
| EP | 2 377 480 A1 | 10/2011 |
| EP | 2 554 132 A1 | 2/2013 |
| EP | 2 674 124 A1 | 12/2013 |
| JP | H-6-30947 A | 2/1994 |
| JP | H-11-505163 A | 5/1999 |
| JP | 2000-51227 A | 2/2000 |
| JP | 2004-524924 A | 8/2004 |
| JP | 2004-527360 A | 9/2004 |
| JP | 2007-532244 A | 11/2007 |
| JP | 4156134 B2 | 7/2008 |
| JP | 2010-537792 A | 12/2010 |
| JP | 2013-509982 A | 3/2013 |
| SU | 1223 895 A | 4/1986 |
| WO | WO 2005/099593 A1 | 10/2005 |
| WO | WO 2009/033057 A2 | 3/2009 |
| WO | WO 2011/059491 A1 | 5/2011 |

* cited by examiner

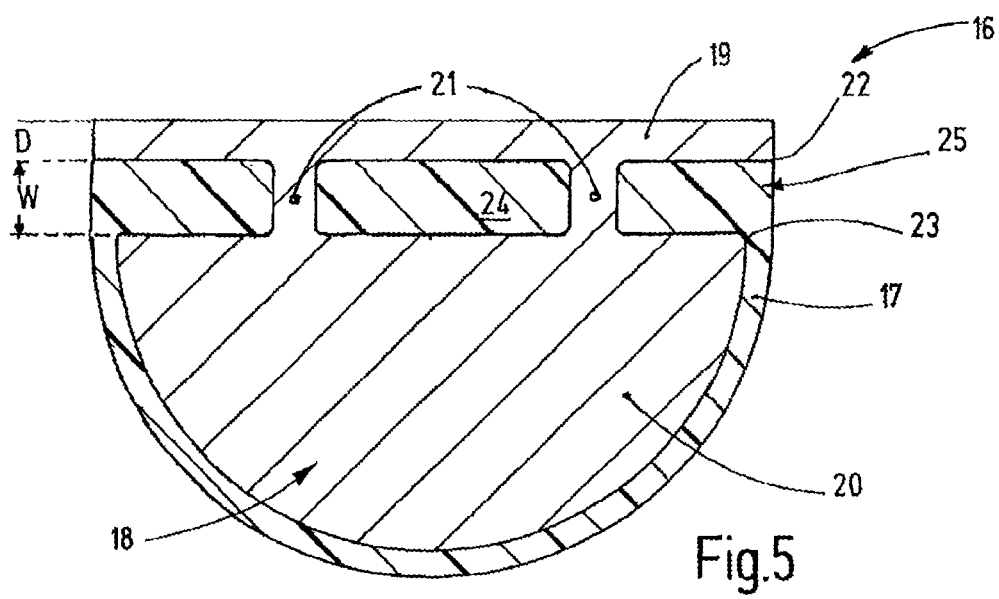
Fig.5
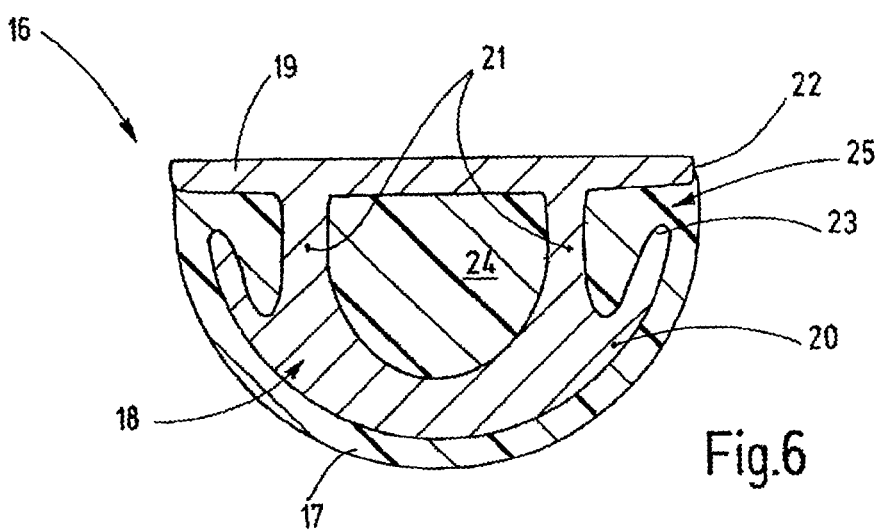
Fig.6
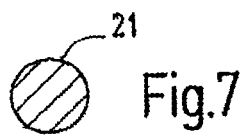
Fig.7
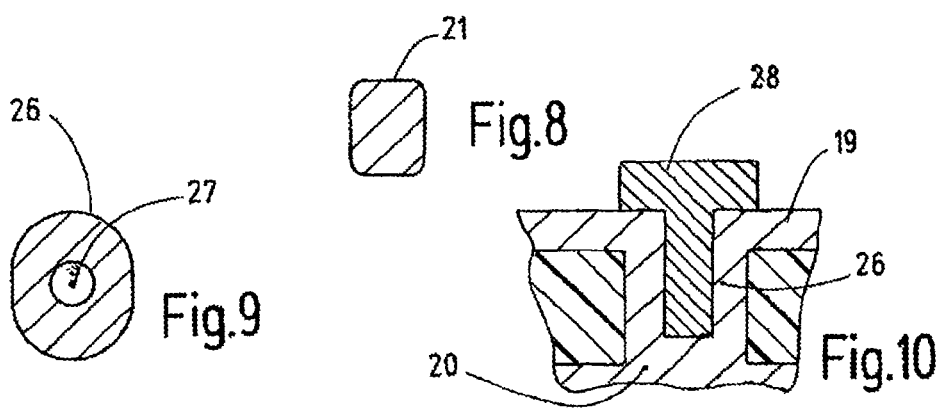
Fig.8
Fig.9
Fig.10

SURGICAL INSTRUMENT COMPRISING ELECTRODE SUPPORT

This application is a divisional of U.S. patent application Ser. No. 14/619,890, filed Feb. 11, 2015, now U.S. Pat. No. 9,848,939, issued Dec. 26, 2017, which claims priority to European Patent Application No. 14154832.1 filed Feb. 2, 2014, the entirety of each of which is hereby incorporated by reference.

TECHNICAL FIELD

Embodiments of the invention relate to a surgical instrument for the electrosurgical monopolar or bipolar application of current to biological tissue, in particular a sealing instrument.

BACKGROUND

Instruments for the coagulation of biological tissue between two branches of a tool comprising at least one movable branch are known from the state of the art. For this purpose, EP 2 554 132 shows an instrument, the branches of which in each case comprise an electrode support and a thin plate-shaped electrode. The electrode support can consist of a massive metal part or of a plastic-coated metal part. The electrode is connected to the electrode support via a plurality of point-like welded connections. On the one hand, a reliable mechanical connection and, on the other hand, only a small heat transfer between the electrode and the electrode support is to be attained with this. Even though the seams have only a small diameter, they also have only a small length (expansion in heat flow direction), which limits their effect as heat barrier.

On the one hand, a mechanically stable and electrically reliable connection must be created between the electrode plate and the electrode support. On the other hand, the heat transfer is to be minimized.

SUMMARY

Based on this, it is the goal of embodiments of the invention to specify an improved surgical instrument, in particular comprising an improved branch for the use in open surgery, for laparoscopic and endoscopic use.

This object is solved by means of the surgical instrument, in particular with an electrosurgical instrument according to embodiments described herein.

The instrument according to embodiments of the invention comprises a branch, in the case of which the electrode support and the electrode plate are connected to one another seamlessly in one piece via a plurality of webs. The webs and also the transitions between the webs and the electrode support on the one hand, and the electrode plate on the other hand, are thus embodied of material with the same composition and structure without any transition. The preferred material thereby comprises sufficient electrically conductive characteristics, so that current can be applied to tissue by means of the electrode plate. Seams, as they are created by remelting parts of an electrode plate or of a branch support when made of a plurality of individual parts, are completely missing here. This concept provides for the minimizing of the dimensions of the webs to what is necessary electrically, mechanically and with regard to production. It furthermore provides for a minimizing of the length of the webs. Preferably, the length of a web is at least as large as the square root of its average cross sectional surface. More preferably, the length of a web is at least as large as the square root of its smallest cross sectional surface. Due to these measures, the heat transfer resistance from the electrode plate to the electrode support can be maximized. This is in particular the case, when a plastic, which is injected into the slit between the electrode support and the electrode plate, supports the mechanical connecting effect of the webs or also takes it over to a large extent.

The embodiment of a heat resistance, which is as large as possible, between the electrode plate and the electrode support can be used to keep the side of the branch, which faces away from the electrode plate, as cool as possible during operation. While the tissue seized between electrodes and thus also the electrode plate, which is in contact therewith, can heat up to temperatures of above 100° C., the electrode support and thus the outer side of the branch on the rear side can be kept at a lower temperature, which prevents or at least reduces damages to the tissue, as compared to the electrode plate. Tissue damages can already occur starting at 40° C., but at least starting at 60° C., for example. This provides for a very precise and specific tissue treatment even in the case of difficult surgeries and in the direct vicinity to sensitive tissue, such as nerve tissue, for example.

In the case of a specific embodiment, the webs are arranged so as to be spaced apart from the opening of the slit. Through this, the small heat flow from the electrode plate to the electrode support is kept away from the edge of the electrode support, so that the edge temperature of the branch can be lowered further.

The distance of the webs from the edge contour of the electrode support can furthermore be larger than the width of the slit. This promotes the above-mentioned effect.

The webs can comprise a round cross section. However, it is also possible that they comprise a differing non-round cross section, wherein the cross sections of all of the webs can be embodied equally or also in a different manner. The cross sections of the webs can furthermore comprise the same or different orientations, so as to maximize the cross stability of the support of the electrode plate at the electrode support, for example.

The webs can comprise a largest diameter, which is smaller than the slit width. The webs are then very delicate and have a small heat conductivity. If the electrode support comprises a bowl-shaped cross section, the length of the individual webs can be maximized, which further increases the heat resistance.

The electrode plate can furthermore transition in one piece, seamlessly into the electrode support at one end. The electrode plate can be a flat, possibly profiled part. The design of the electrode surface, which faces the tissue, can be designed freely, depending on the application. In particular, the electrode plate can comprise a circumferential edge, which reduces the slit width at the opening of the slit.

Preferably, the electrode support, the webs and the electrode plate are produced in an additive or generative production method, respectively. Preferably, they thereby consist of a homogenous material. In particular the selective laser melting (SLM) is suitable as additive production method, in the case of which the electrode plate, the webs as well as the electrode support are made of metal powder by means of laser sintering or laser melting, respectively. The electrode plate, the webs and the electrode support thus have a homogenous fine structure. Due to the material and the method, the material stabilities, which can be attained, are high and can be compared to casting methods. In the case of structures comprising only a few undercuts, the metal injection molding method, MIM method, can also be considered as further production method. An increased surface roughness of the webs, of the electrode support and at least of the side of the electrode plate, which faces the electrode support, provides for a solid adhesion of plastic to these surfaces. In particular if the slit formed between the electrode plate and the electrode support is injected with plastic and, if applicable, if the electrode support is also otherwise insert molded or coated with plastic, respectively, an firm metal-plastic connection is attained. This is advantageous in particular with regard to the hygienic demands on surgical instruments as well as with regard to possible cleaning and sterilization cycles, in the case of which the instrument, in particular the branch, is subjected to high thermal and also chemical stresses.

The insert molding of the electrode support with plastic effects at least an electric and, depending on the plastic thickness, also a noticeable thermal insulation, which is advantageous.

The plastic insert molding can further be used for providing a mechanical calibration of the electrode support, for example in the area of its bearing bore. For this purpose, the electrode support comprises a cross passage, the accuracy of which is of secondary importance in response to the production. The accurate bearing bore can then be attained in response to the insert molding of the electrode support with plastic in the plastic injection mold by using a mold core, which extends through the cross opening of the electrode support and which accurately determines the position of the bearing bore in the plastic. Every time the above and below description as well as the claims refer to plastic or plastic material, respectively, this also comprises materials comprising insulating characteristics, which cannot be assigned to the group of the plastic materials.

Further details of advantageous embodiments of the invention are the subject matter of claims, the description and/or the drawings.

BRIEF DESCRIPTION OF THE DRAWINGS

FIGS. 5 and 6 show cross sections of different embodiments of branches according to FIGS. 3 and 4, FIGS. 7 and 8 show cross sections of webs in different embodiments, FIG. 9 shows a cross section of a hollow web, FIG. 10 shows a longitudinal section through a hollow web comprising a spacer element accommodated therein.

DETAILED DESCRIPTION

Figure 1:
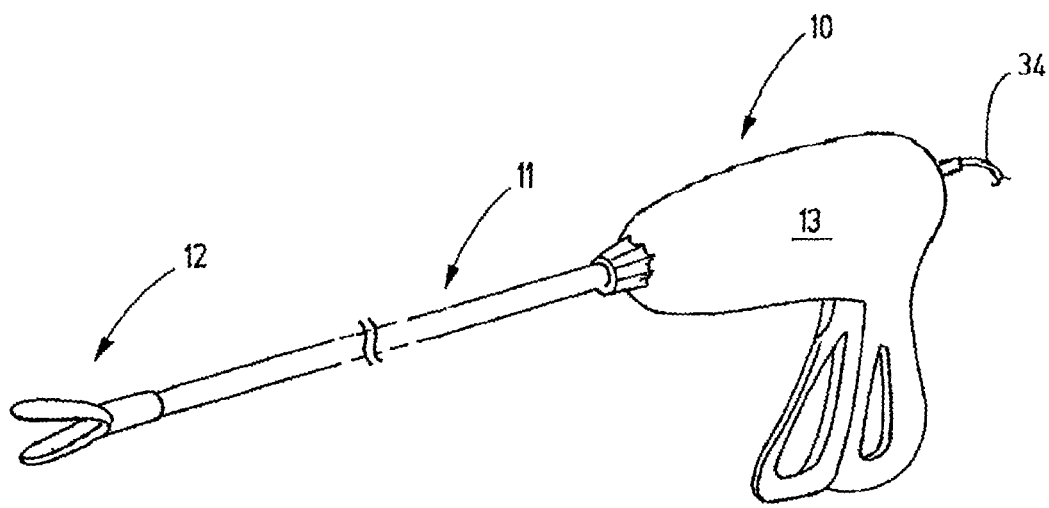
FIG. 1 shows the instrument according to an embodiment of the invention in perspective overview illustration.

By way of example, the instrument 10 illustrated in FIG. 1 is illustrated as tube shaft instrument for use in open and/or laparoscopic surgery. It comprises a shaft 11, at the distal end of which a tool 12 is arranged. A housing 13, which comprises a handle 14 and which is connected to the proximal end of the shaft 11, serves to handle the instrument 10. The instrument 10, however, can also be embodied as flexible endoscopic instrument, wherein the tool 12 as well as the shaft 11 are then correspondingly small and delicate and the shaft 11 is flexible. The basic description below also applies for such embodiments.

Figure 2:
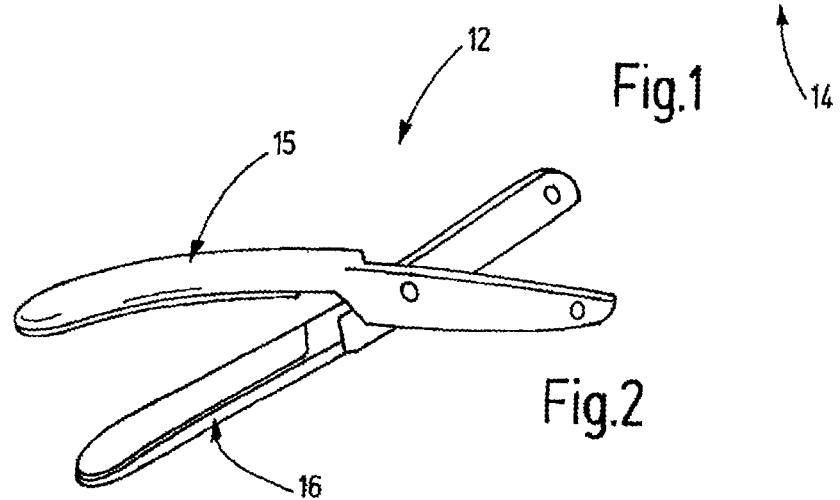
FIG. 2 shows the tool of the instrument according to FIG. 1 in perspective overview illustration.

FIG. 2 illustrates the tool 12 with two branches 15, 16, which cooperate in the manner of pliers and which, on principle, comprise the same basic design. The following description of the branch 16 illustrated in FIGS. 3 to 6 thus applies accordingly for the branch 15.

Figure 4:
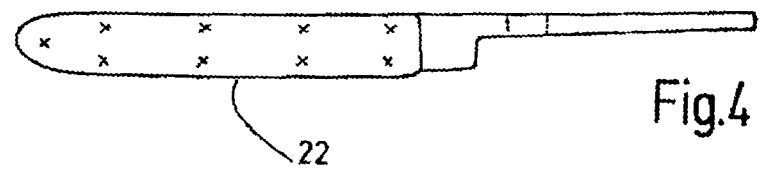
FIG. 4 shows the branch according to FIG. 3 in top view.

The branch 16 is illustrated in FIG. 4 by omitting its plastic jacket 17, which, in turn, is illustrated in more details in FIG. 5.

Figure 3:
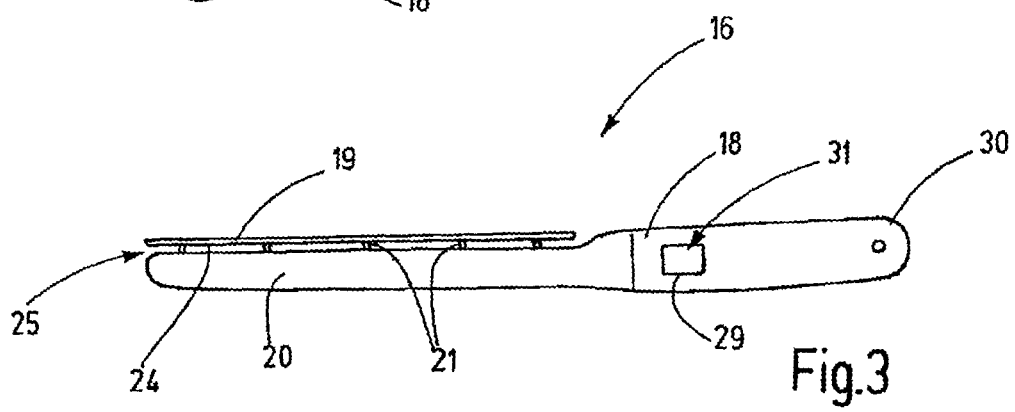
FIG. 3 shows a branch of the tool according to FIG. 2 in side view.

FIGS. 3 and 4 thus only illustrate the part of the branch 16, which consists of metal. This metal part 18 is divided into an electrode plate 19, which is embodied in the manner of a thin, possibly formed sheet metal plate, an electrode support 20 and a plurality of connecting webs 21, which are arranged therebetween. The electrode plate 19, the electrode support 20 and the webs 21 are embodied seamlessly from a homogenous material in one piece. As is illustrated, the electrode plate 19 can be embodied so as to be flat and, according to FIG. 4, so as to be stretched in a straight manner. However, it can also be embodied so as to be curved in one or a plurality of directions, if this is desired for a certain use. For example, the electrode 19, in top view, can be embodied so as to differ from FIG. 4, following a curve. In addition, it can be embodied so as to be bowl-shaped in a convex or concave manner and, if desired, it can be embodied so as to be profiled in each of the mentioned cases. The profile can consist of teeth, cross webs, longitudinal ribs along the edge contour 22 or the like. It is further possible to provide the electrode plate 19 with a continuous slit or with a slit, which ends shortly upstream of the distal end, for accommodating a blade. In any event, the electrode plate 19 comprises an edge contour 22, which extends along a side, then across the distal end and then along the opposite side (see also FIG. 5), which is preferably embodied so as to run parallel to an edge contour 23 of the electrode support 20.

As is shown in FIG. 5, the electrode support 20 can be embodied as full profile and, according to FIG. 3, can extend at a constant or also at a changing distance to the electrode plate 19. Between one another, the electrode plate 19 and the electrode support 20 define a slit 24, the opening 25 of which is defined all around along the edge contours 22 and 23 between the latter. As can be seen, the opening 25 can comprise a homogenous width W all around, measured between the edge contours 22 and 23. According to FIG. 5, the edge contour 23, based on the edge contour 22, can additionally be offset towards the inside. The electrode plate 19 projects beyond the electrode support 20 here. The ratios, however, can also be reversed. The electrode plate 19 can comprise a thickness D, which is smaller than the width W of the opening 25 of the slit 24 (FIG. 5).

As shown in FIG. 5, the webs 21 are preferably spaced apart from the opening 25 and thus from the edge contours 22, 23. The webs 21 merge seamlessly into the electrode plate 19. The webs 21 also merge seamlessly into the electrode support 20. The length of the webs 21 is preferably at least as large as the width of the opening 25.

Figure 12:
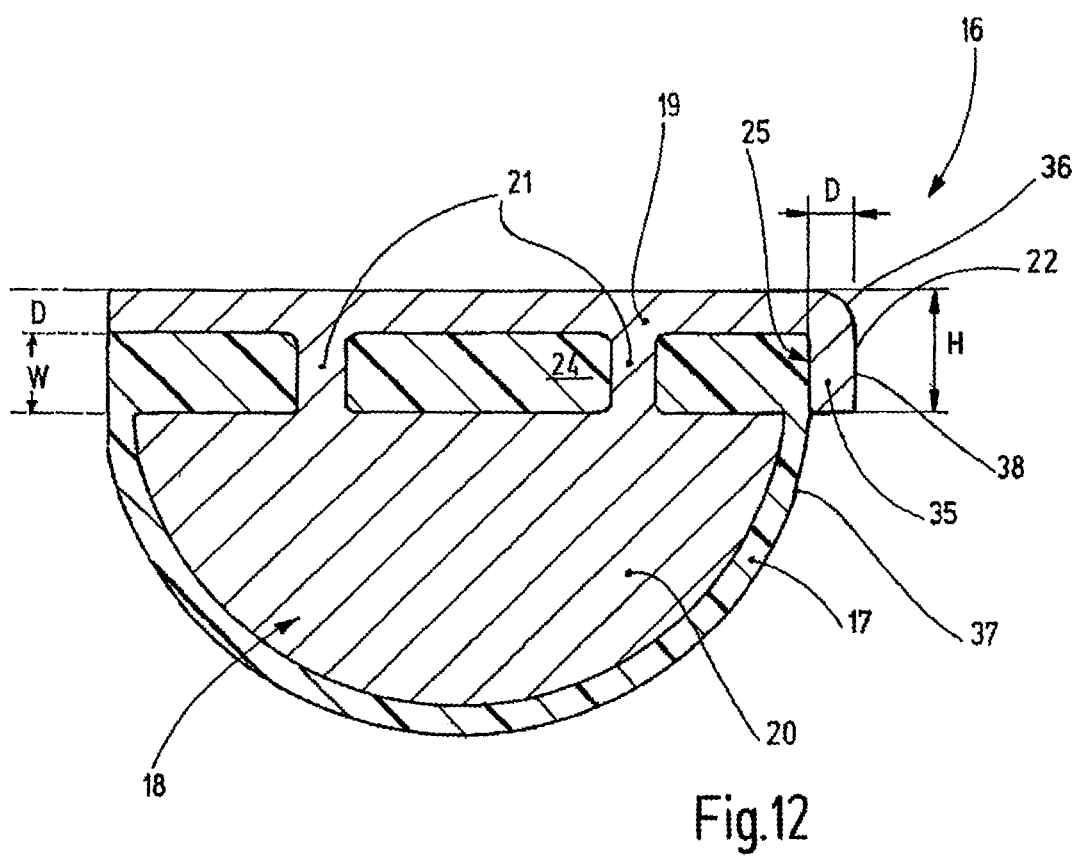
FIG. 12 shows a cross section of a modified embodiment of a branch according to an embodiment of the invention.

As shown in FIG. 12, the edge contour 22 of the electrode plate 19 can comprise an extension in the form of a projection 35. This projection 35 is arranged at an angle, preferably at a 90° angle, to the plane of the electrode plate 19 and can partially or completely project beyond the opening 25 of the slit 24. The projection 35 can comprise a height H, which is larger than the thickness D of the electrode plate. The height H of the projection 35 can lie within the range of between 0.3 mm and 0.5 mm, preferably 0.4 mm. The thickness of the projection 35 is preferably equal to the thickness D of the electrode plate 19, but can also be slightly larger or smaller. The projection 35 projects beyond the plastic jacket 17, so that the outer flange 37 of the plastic jacket 17 is arranged at a distance to the outer flange 38 of the projection 35. The outer flange 37 of the plastic jacket 17 is arranged closer to the center of the electrode support 20 as compared to the outer flange 38 of the projection 35. The distance between the outer flange 37 of the plastic jacket 17 and the outer flange 38 of the projection 35 is preferably slightly smaller than the thickness D of the projection 35. The transition area 36 from projection 35 to the electrode plate 19 is preferably embodied so as to be rounded so as to protect the tissue. As illustrated in FIG. 12 at a location (on the right-hand side of the figure), the geometry of the edge contour 22 with the projection 35 of a branch 16 extends preferably along a side, then across the distal end and then along the opposite side of the electrode plate 19. This edge contour 22 can comprise the same geometry continuously throughout, it can also comprise breaks in the form of recesses. As described, an edge contour 22 with projection 35 supports the reliable closing of vessels.

The metal body described insofar, which consists of electrode plate 19, electrode support 20 and webs 21, is preferably produced in an additive production method, for example powder-metallurgically by means of laser sintering or laser melting (SLM method). The webs 21 thus have the same material structure as the electrode plate 19 and the electrode support 20 as well as the same stability. The diameters of the webs 21 can be smaller than the length of the webs 21. The cross sections thereof can be embodied so as to be round or substantially circular, respectively, for example, as illustrated in FIG. 7, or can be embodied so as to be non-round in accordance with FIG. 8. High mechanical stability can be paired with a low heat conductivity can be paired in this manner.

Preferably, the slit 24 is filled with a plastic, which merges into the plastic jacket 17 on the outside. The slit 24 is thus closed, so that the permeation of liquid, bacteria or other biological materials is counteracted. The plastic furthermore adheres to the surfaces, which face one another and which define the slit 24. In addition, the plastic jacket 17 can adhere well to the rear side of the electrode support 20, the lower side in FIG. 5. The plastic jacket 17 effects an electrical and thermal insulation of the electrode support 20 against surrounding tissue. The plastic in the slits 24 effects a mechanical support of the electrode plate 19, as well as a thermal shielding thereof against the electrode support 20.

FIG. 6 illustrates a modification of the cross section of the branch 16, in particular with regard to the embodiment of the webs 21 and of the electrode support 20. As illustrated, the latter can be embodied approximately in a bowl-shaped manner, whereby the length of the webs 21 and the inner width of the slit 24 become larger. The webs 21 can be embodied in a cylindrical manner or also so as to thicken at one or both ends. Otherwise, the above description applies accordingly based on the same reference numerals.

Instead of delicate webs 21, hollow webs 26 according to FIGS. 9 and 10 can also be used at one or a plurality of locations. These hollow webs 26 can enclose a channel 27, which breaches the upper side of the electrode plate 19, for example, and which is suitable to accommodate a spacer 28, for example made of plastic, ceramic or the like. According to FIG. 10, the hollow webs 26 can form a connection between the electrode plate 19 and the electrode support 20.

However, they can also be embodied as blind pin, that is, they can end at a distance upstream of the electrode support 20. In this case, they do not contribute to the electrical and mechanical connection between the electrode plate 19 and the electrode support 20. The connection is then taken over completely or partially by other webs 21 and/or by the plastic arranged in the slit 24.

Figure 11:
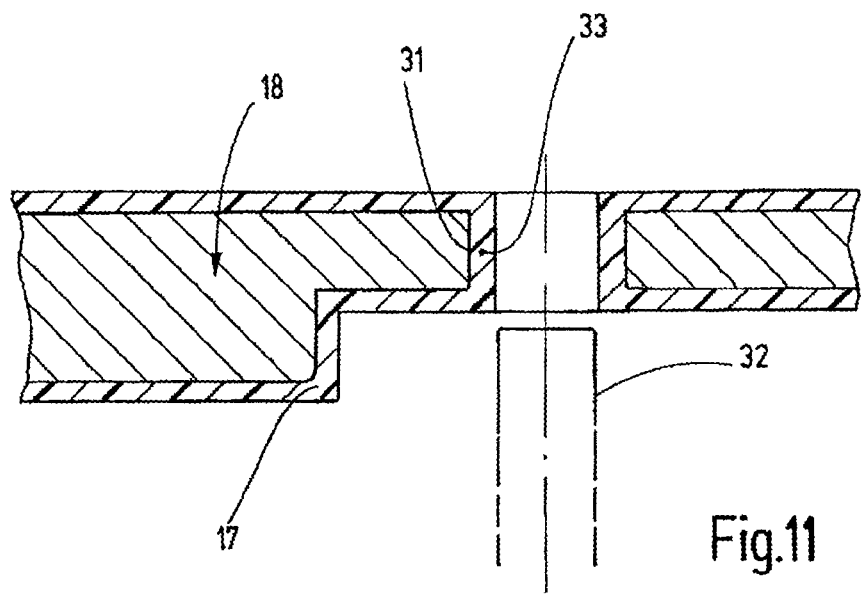
FIG. 11 shows a horizontal section through a branch according to FIG. 3 or 4 comprising a plastic coating in the area of the bearing bore.

The plastic jacket 17 can extend beyond the electrode support 20 to a joint section 29 (FIG. 3) and, if applicable, further to an operating connection 30. The joint section 29 serves to embody a pivot joint so as to be able to open and close the branches 15, 16 in the manner of pliers. For this purpose, the joint section 29 is provided with a through opening 31, which extends across the joint section 29 and which can be embodied so as to be round or non-round and which preferably comprises a diameter, which is larger than the outer diameter of a bolt 32, which is provided for support (FIG. 11). The plastic jacket 17 preferably extends through the through opening 31 and forms a bearing sleeve 33 at that location. This bearing sleeve 33 is an integral component of the plastic jacket 17. It insulates the metal part 18 against the bolt 32 and at the same time centers the latter in the through opening 31, namely largely independent from production tolerances of the metal part 18.

The instrument 10, which has been described insofar, operates as described below.

The electrode plates 19 of the two branches 15, 16 are connected to an electrical power source, for example an HF generator, via lines, which lead through the shaft 11, and via a connecting cable 34. In response to activation, a voltage is present, so that power is applied to the tissue seized between the branches 15, 16. For this purpose, a hand lever is operated on the handle 14, so as to close the branches 15, 16 and so as to seize tissue between them. By supplying power, the temperature in the tissue rises, whereby it coagulates. The temperature of the electrode plates 19 thus partially also rises beyond boiling temperature. The heat, however, is largely limited to the electrode plate 19. The plastic arranged in the slit 24 comprises a heat conductivity, which is smaller than the heat conductivity of the electrode plate 19. Due to their small cross sectional surface, the webs 21 additionally transfer only little heat energy, so that the electrode support 20 remains cool for the most part. The preferred large heat capacity of the electrode support 20 accommodates the small transferred heat quantities with only a small temperature increase. This effect can be intensified in that heat-buffering materials, in particular latent heat stores, for example wax, are arranged in one or a plurality of hollow chambers of the plastic and/or of the electrode support 20, wherein the storage temperature is preferably defined to a low temperature range, which does not damage the issue, of 60° C., for example, or less. The outer sides of the branches 15, 16 can thus be kept sufficiently cool even in response to a longer use.

A branch 16 of an instrument 10 comprises a metal part 18, which is embodied in one piece seamlessly, which comprises the electrode support 20 as well as the electrode plate 19 and connection webs 21, which are present. Preferably, this metal part 18 is produced in an additive production method, for example selective laser melting (SLM). By eliminating welds or seams between the electrode plate 19 and the electrode support 20, connections, which conduct heat poorly and which, simultaneously, are mechanically very stable, can be created by means of the webs 21. The branch is suitable for instruments for open surgery as well as for laparoscopic and flexible endoscopic instruments.

What is claimed as new and desired to be protected by Letters Patent of the United States is:

1. An electrosurgical instrument comprising:
a first branch having a first metal part, the first metal part comprising:
 a first sealing electrode; and
 a first hinge bore;
a second branch having a second metal part, the second metal part comprising:
 a second sealing electrode; and
 a second hinge bore; and
a bolt arranged within the first hinge bore and second hinge bore to rotatably couple the first branch to the second branch,
wherein the first hinge bore has a first plastic jacket that coats and extends through the first hinge bore to form a bearing sleeve configured to center the bolt at an axis in the first hinge bore by compensating for production tolerances in the first metal part and is coextensive with a plastic electrode sleeve enveloping at least a distal edge of the first sealing electrode.

2. The electrosurgical instrument of claim 1, wherein the first plastic jacket is configured to insulate the first metal part from the bolt.

3. The electrosurgical instrument of claim 1, wherein the first plastic jacket is configured to electrically isolate the first branch from the second branch.

4. The electrosurgical instrument of claim 1, wherein the second sealing electrode seals tissue when operated in conjunction with the first sealing electrode.

5. The electrosurgical instrument of claim 1, wherein the first and second metal parts further comprise, respectively, first and second electrode carriers coupled to the first and second sealing electrodes, respectively.

6. The electrosurgical instrument of claim 1, wherein the first plastic jacket further extends to cover at least a portion of the first metal part other than the first hinge bore.

7. The electrosurgical instrument of claim 1, wherein the first plastic jacket is arranged to improve the accuracy of the first hinge bore to thereby align the first sealing electrode and second sealing electrode.

8. The electrosurgical instrument of claim 1, wherein the first plastic jacket is configured to mechanically calibrate the first hinge bore.

9. The electrosurgical instrument of claim 1, wherein the first plastic jacket is configured to rotate with the first hinge bore exclusive of any rotation of the bolt.

10. The electrosurgical instrument of claim 1, wherein the bearing sleeve is configured to center the bolt in the first hinge bore during rotation of the bolt in the bearing sleeve.

11. The electrosurgical instrument of claim 1, wherein the second hinge bore has a second plastic jacket that coats and extends through the second hinge bore, and wherein the first hinge bore and second hinge bore are configured to form the bearing sleeve, and the bearing sleeve is configured to center the bolt at an axis in first hinge bore and second hinge bore by compensating for production tolerances in at least one of the first metal part and the second metal part.

12. The electrosurgical instrument of claim 11, wherein the second plastic jacket further extends to cover at least a portion of the second metal part other than the second hinge bore.

13. The electrosurgical instrument of claim 11, wherein the second plastic jacket is arranged to improve the accuracy of the second hinge bore to thereby align the first sealing electrode and second sealing electrode.

14. The electrosurgical instrument of claim 11, wherein the second plastic jacket is configured to mechanically calibrate the second hinge bore.

15. The electrosurgical instrument of claim 11, wherein the second plastic jacket is configured to rotate with the second hinge bore exclusive of any rotation of the bolt.

16. The electrosurgical instrument of claim 11, wherein the bearing sleeve is configured to center the bolt in the second hinge bore during rotation of the bolt in the bearing sleeve.

17. The electrosurgical instrument of claim 1, wherein at least one of the first hinge bore and second hinge bore is round.

18. The electrosurgical instrument of claim 1, wherein at least one of the first hinge bore and second hinge bore is non-round.

19. The electrosurgical instrument of claim 1, wherein at least one of the first hinge bore and second hinge bore is rectangular.

* * * * *